United States Patent [19]

Zweigle

[11] Patent Number: 4,849,415

[45] Date of Patent: Jul. 18, 1989

[54] SUSTAINED RELEASE COMPOSITIONS

[75] Inventor: Maurice L. Zweigle, Northport, Mich.

[73] Assignee: The Dow Chemical Company, Midland, Mich.

[21] Appl. No.: 690,802

[22] Filed: Jan. 11, 1985

Related U.S. Application Data

[63] Continuation-in-part of Ser. No. 471,596, Mar. 3, 1983, abandoned.

[51] Int. Cl.[4] .................. A01N 29/02; A01N 57/00; A01N 57/10
[52] U.S. Cl. ........................... 514/89; 424/78; 514/147; 514/740; 514/746
[58] Field of Search ............... 514/89, 147; 424/78

[56] References Cited

U.S. PATENT DOCUMENTS

| | | | |
|---|---|---|---|
| 3,424,842 | 1/1969 | Nurnberg | 424/94 |
| 3,761,589 | 9/1973 | Balassa | 514/89 |
| 4,048,315 | 9/1977 | Bredereck et al. | 544/223 |
| 4,102,991 | 7/1978 | Kydonieus | 424/27 |
| 4,174,445 | 11/1979 | Mohring et al. | 544/223 |
| 4,220,663 | 9/1980 | Schulze et al. | 514/89 |
| 4,244,836 | 1/1981 | Frensch et al. | 252/316 |
| 4,303,640 | 12/1981 | Fuyama et al. | 424/78 |
| 4,322,413 | 3/1982 | Baumann et al. | 548/112 |
| 4,345,078 | 8/1982 | Hofer et al. | 544/244 |
| 4,348,385 | 9/1982 | Synek | 514/89 |
| 4,363,804 | 12/1982 | Fawcher | 514/89 |
| 4,429,120 | 11/1984 | Dehnke | 536/91 |
| 4,502,888 | 3/1985 | Leng et al. | 106/170 |

*Primary Examiner*—Allen J. Robinson

[57] ABSTRACT

Compositions capable of the sustained release of active organic agents are made from an aqueous dispersion of a water-insoluble cellulose ether which cellulose ether particles have reversibly diffused therein the active agent. The dispersions may be used as dispersions, dewatered to form a powder, or coalesced to form films or other articles all of which are capable of sustained release of the active agent.

9 Claims, No Drawings

SUSTAINED RELEASE COMPOSITIONS

REFERENCE TO RELATED APPLICATION

This Application is a continuation-in-part of U.S. Pat. application Ser. No. 471,596, filed Mar. 3, 1983, now abandoned.

BACKGROUND OF THE INVENTION

This invention relates to compositions for the sustained release of organic compounds.

The usefulness of many organic compounds, such as insecticides, herbicides, antimicrobials, fertilizers, medicines and the like, would be greatly improved if an inexpensive, effective system for the continual release of such compounds were available. Many organic compounds, for example, are volatile or unstable in the environment in which they are employed. When large doses of such compounds are used, much of the compound volatilizes or decomposes before performing its desired function. Accordingly, it would be desirable to administer such compounds in a form which reduces the rate of volatilization or decomposition thereof while maintaining effective levels of the compound in the system treated therewith. Other organic compounds are effective in very low concentrations, and are most effectively employed when such low effective concentrations are continually released into the system being treated. Moreover, the use of still other such compounds would be increased if they could be employed as a solid, such as a film or powder.

Various processes are known in which polymeric materials are employed in conjunction with organic compounds to form sustained release systems. For example, in U.S. Pat. Nos. 3,795,744 and 3,857,964, it is taught to form a coating of a polymeric material such as a cellulose ether around the organic compound to be released therefrom. The organic compound is released by the physical destruction of the polymeric coating or by the leaching of the organic compound through the polymeric coating. Unfortunately, due to the limitations in size and physical form of such coated compositions, the use thereof is greatly restricted. In addition, the coating operation must be carefully controlled in order to obtain a product having predictable and desirable release characteristics.

Another conventionally employed sustained release system comprises forming a solid matrix of a binder material such as a cellulose ether, which matrix has dispersed therein the organic compound to be released. While such matrix systems are somewhat useful in the preparation of pharmaceutical tablets, the size of such matrix systems often precludes the use thereof in other applications. In addition, the active agent is often unevenly distributed in such matrix systems, causing uneven release of the active agent.

Accordingly, an easily prepared sustained release system for organic compounds, which system has a physical form which is amenable to a variety of uses would be highly desired.

SUMMARY OF THE INVENTION

The present invention is an aqueous dispersion comprising a plurality of solid particles of a water-insoluble, organophilic cellulose ether, said particles having reversibly diffused therein an active agent which exhibits a greater affinity for the cellulose ether than for the aqueous phase. Under suitable conditions, the active agent diffuses out of the cellulose ether particles, thereby producing a continuous, sustained release of the active agent. The dispersions of this invention can be employed while in the form of a dispersion or may be dewatered using any suitable process to produce a powdery material having sustained release properties. In addition, the dispersions of this invention may be coalesced to form films or other articles which slowly release the active agent.

In another aspect, this invention is a dispersion of plasticized, polymeric particles for the sustained release of an active agent. The dispersion comprises:
(a) a continuous aqueous phase having dispersed therein,
(b) a plurality of particles; which particles are comprised of
  (1) a water-insoluble thermoplastic cellulose ether polymer;
  (2) a plasticizing composition comprising an amount of a water-soluble salt of a fatty acid sufficient to stabilize the dispersion, said fatty acid being one which is a plasticizer for the cellulose ether polymer; and
  (3) an active agent reversebly diffused into the particles wherein said active agent is an organic compound or composition which exhibits a greater affinity of the cellulose ether than the aqueous phase.

DETAILED DESCRIPTION OF THE INVENTION

The cellulose ether employed is one which is insoluble in water and one in which the active agent can become reversibly diffused. In general, the substituent groups on the cellulose ether are chosen such that it renders the cellulose ether somewhat organophilic. Generally, organophilic cellulose ethers are organosoluble and demonstrate a strong tendency to associate with organic compositions. The organosolubility of cellulose ethers ranges from swelling and forming reversible gels to complete dissolution. Exemplary cellulose ethers useful herein include the alkyl cellulose ethers, especially $C_2$–$C_4$ alkyl cellulose ethers; 2-hydroxyalkylcellulose ethers, especially $C_4$-hydroxyalkylcellulose ethers; mixed alkylhydroxyalkylcellulose ethers, especially $C_2$–$C_4$ alkyl $C_3$–$C_4$ hydroxyalkylcellulose ethers; and the like. In general, both the organophilic character and the water insolubility of these cellulose ethers increase with increasing size of the substituent alkyl or hydroxyalkyl groups, as well as with increasing amounts of such substitution. The manipulation of the amounts and types of substitution to prepare a water-insoluble product is within the skill of those familiar with preparing cellulose ethers, and an exhaustive enumeration of suitable cellulose ethers is not considered to be necessary herein. Most preferred are ethylcellulose, ethylmethylcellulose, ethylhydroxypropylmethylcellulose ethers such as described in U.S. Pat. No. 4,429,120 to Dehnke, herein incorporated by reference.

The cellulose ether is dispersed as a plurality of finely divided particles into a continuous aqueous phase. Aqueous dispersion of water-insoluble cellulose ethers such as ethylcellulose and methods for their preparation are known in the art and are described, for example, U.S. Pat. Nos. 2,345,879, 4,177,177 and 4,502,888, herein incorporated by reference. At least sufficient water to form a continuous aqueous phase is employed, and more typically, sufficient water is employed to form a dispersion containing about 5 to about 40 weight percent solids. The aqueous phase may contain, in addition to water, a comiscible or water-soluble organic compound or polymer, which may be present for purposes such as increasing or decreasing the viscosity of the aqueous phase, increasing the volatility thereof, increasing the compatibility thereof with additional, optional components of the dispersion, and the like. The use of such organic compound or polymer is beneficial as long as the active agents therein have a greater affinity for the cellulose ether particles than the aqueous phase. Examples of such organic compound or polymer include thickeners such as polyvinyl alcohol and water-soluble cellulose ethers; water-miscible organic compounds such as acetone, ethanol, methanol, and the like.

The cellulose ether is dispersed into the aqueous phase as a plurality of finely divided particles. While a suspending agent is not necessarily employed if the cellulose ether particles are sufficiently small or the viscosity of the aqueous phase sufficiently high, the preparation of such finely divided cellulose ether particles is difficult and a high viscosity aqueous phase is not generally desirable. Accordingly, a suspending agent is generally employed herein. In general, the choice of suspending agent is not especially critical as long as the dispersion is stabilized therewith, i.e., the dispersed particles do not substantially agglomerate or settle out of aqueous phase. However, the suspending agent must be chosen such that it is substantially inert to the active agent employed in the dispersion. For example, certain suspending agents, such as those containing weak acid groups, are primarily useful at high pH. Such suspending agents cannot be employed when the active agent is reactive or unstable at high pH. Similarly, suspending agents which are useful at low pH are not suitably employed when the active agent degrades or reacts at such low pH. Exemplary such stabilizers include surfactants, such as alkyl sulfonates and sulfates, alkyl benzyl sulfates and sulfonates, sulfonated condensation products of phenols or alkylphenols with ethylene oxide or propylene oxide, condensation products of long chain aliphatic alcohols with ethylene oxide, polymeric stabilizers such as polyvinyl alcohol, polyethylene glycol, carboxymethylcellulose or carboxymethylmethylcellulose and the like.

The suspending agent, when employed, is generally present in an amount from about 0.5 to about 35 weight percent based on the weight of the dispersed polymer particles.

The dispersions of this invention further contain a quantity of an active agent which is reversibly diffused in the cellulose ether particles. As used herein, the term "active agent" refers to an organic compound or mixture of organic compounds which is to be controllably released by the dispersion. Said active agent is an organic compound or composition which is capable of becoming reversibly diffused within the cellulose particle and which has a greater affinity for the cellulose ether than the aqueous phase. By "reversibly diffused in the cellulose ether particles" is meant that the active agent is associated with the cellulose ether particles in such a manner that under suitable conditions it can be released therefrom in its active form. The nature of the association of the active agent with the cellulose ether particles is not especialy critical as long as it is reversible and may be, for example, an absorption, an adsorption, or a dissolution of the active agent into the cellulose ether particles.

Water-insoluble cellulose ethers are compatible with a wide range of organic compounds. Any such organic compound, or mixture of such compounds, which is readily diffused into and retained by the cellulose ether particle, may be employed as the active agent herein. In addition, other organic compounds or mixtures thereof which have only limited compatibility with the cellulose ether, (i.e., those which are not readily diffused into the cellulose ether or which, when diffused therein, rapidly diffuse back out of the cellulose ether), can be used herein if employed in conjunction with a compatibilizing material which increases the compatibility of the organic compound and the cellulose ether. The compatibility of the organic compound and organophilic cellulose ether is related to the tendency of the cellulose ether to associate with the organic compound. Increasing the compatibility means that the cellulose ether's solubility in and/or tendency to associate with the organic compound is increased. Said compatibilizing agent is an organic compound or polymer which is highly compatible with both the cellulose ether and the active agent, and which (a) enables the active agent to become more readily diffused into the cellulose ether particles, and/or (b) enables the active agent to diffuse out of the cellulose ether particles at a desirable rate under the conditions of use. For example, chlorpyrifos may be desirably employed as the active agent herein, but it is not sufficiently compatible with the cellulose ether to be diffused into the cellulose ether particles in useful quantities. The small quantity of chlorpyrifos which becomes diffused into the cellulose ether particles rapidly diffuses back out. However, when a material such as dibutylphthalate is employed as a compatibilizing material, significant quantities of chlorpyrifos can be diffused into the cellulose ether particles, and the rate of release of the diffused chlorpyrifos is significantly reduced.

Exemplary compatibilizing materials are described hereinafter. The particular choice of compatibilizing material employed, if any, will, of course, depend on the particular active agent employed. In general, compatibility of the active agent with the compatibilizing compound will be within the knowledge of the skilled artisan. Alternatively, the compatibility can often be established by routine experimentation, such as by simply mixing or blending the active agent and the compatibilizing material to see if they form a homogeneous blend. Similarly, optimum amounts of compatibilizing materials employed can be established by simple experiments. In general, however, said compatibilizing agent is advantageously employed in an amount in the range from about 0.5 to about 50, preferably from about 5 to about 30 weight percent based on the weight of the cellulose ether.

The active agent may be, for example, a herbicide, insecticide, nematocide, fungicide, antimicrobial or other biocides, a medication, vitamin, coloring, preservative or any other organic compound or mixture of organic compounds which is advantageously controllably released into the system to be treated therewith. As long as the active agent can become reversibly diffused, either alone, in a solution, or with the use of a compatibilizing agent, into the cellulose ether particles, its structure is not especially critical. Suitable active agents range from comparatively simple molecules, like carbon tetrachloride to complex molecules such as vitamins.

Exemplary herbicides include, for example, alkanolamine salts of dinitro-o-sec-butylphenol, propylene glycol butyl ethers of 2-(2,4,5-trichlorophenoxy) propanolic acid, chlorinated phenoxy acetic acid and salts or esters thereof, salts of 4-amino-3,5,6-dichloropicalinic acid, as well as many other commerically available herbicides.

Suitable insecticides include, for example, chlorpyrifos-(O,O-dialkyl-O-(3,5,6-trichloro-2-pyridyl) phosphorothioate), fenchlorphos-(O-O-dialkyl-O-(2,4,5trichlorophenyl) phosphorothioate) and the like.

Suitable fungicides include 1,3-dichloropropene, trichloronitromethane (chloropicrin), mixtures thereof and the like.

Medications and vitamins may also be employed as the active agent herein. Especially useful are those medications and vitamins which are known to be somewhat unstable in the digestive system and those which are more effectively administered in constant small dosages rather than large intermittent dosages. Of particular interest herein are nitroglycerin and the diverse medications commonly employed in throat lozenges.

Exemplary preservatives include the phenylphenols, chlorinated phenylphenols, chlorinated phenols, cyclopentylphenols, hexamethylenetetraamine-1,3-dichloropropane salt, as well as others.

Any of the commonly employed organic flavorants are suitably employed herein, including, for example, orange oil, lime oil, cherry oil, lemon oil, peppermint oil, spearmint oil, wintergreen oil, licorice and other spices and fruit flavors.

The foregoing list of active agents suitably employed herein is not presented as a complete listing thereof and the beneficial use of many other organic compounds as the active agent will be apparent to one skilled in the art having the benefit of the present specification.

Materials suitably employed as a compatibilizing material include phosphate esters such as tri-(2-ethylhexyl)phosphate, tricresylphosphate and triphenylphosphate; phthalate esters such as benzylmethylphthalate, cyclohexylbutylphthalate, dibutylphthalate, dimethylphthalate, diphenylphthalate, diethoxyethylphthalate and the like; fatty acid, salts and esters thereof; fatty alcohols; vegetable oils such as castor oil and corn oil; glycol esters of carboxylic acids, mineral oils, and the like. In addition, surfactants such as are described in U.S. Pat. No. 4,256,505 to Zweigle (hereinafter incorporated by reference) are also suitable compatibilizing materials. Many of the known plasticizers for water-insoluble cellulose ethers are also useful herein as a compatibilizing material.

Any amount of active agent may be employed in the dispersions of this invention as long as the active agent is diffused into the cellulose ether particles and a stable dispersion is maintained. It is understood that the maximum amount of active agent suitably employed will depend somewhat on the particular active agent cellulose ether and compatibilizing materials, if any, employed. In addition, the amount of active agent will depend somewhat on the amount of active agent desirably released and the rate of release thereof by the cellulose ether particles. Thus, the amount of active agent may range, in general, from about 0.1 to about 200, preferably 5 to 100, more preferably 20 to 50, percent based on the weight of the cellulose ether.

In addition to the foregoing components, a dispersion of this invention may, optionally, contain other ingredients as are commonly employed in polymeric dispersions including, for example, flavorings, preservatives, pigments, fillers and the like. For certain uses, such as when the dispersions of this invention are to be formed into films or molded articles, it may be desirable to employ a plasticizer in the dispersion in order to improve the mechanical properties of the cellulose ether. As taught in U.S. Pat. No. 4,502,888, herein incorporated by reference, a dispersion of plasticized polymeric particles can be prepared. The dispersion comprises a continuous aqueous phase with a plurality of particles dispersed therein. These particles comprise a water-insoluble thermoplastic cellulose ether polymer and a plasticizing composition. The plasticizing composition comprises an amount of a water-soluble salt of a fatty acid sufficient to stabilize the dispersion, and the fatty acid is also a plasticizer for the cellulose ether polymer. According to the invention, the active agent described above can be reversibly diffused into these plasticized polymer particles. Plasticizers for cellulose ethers are well known and include, for example, esters of phthalic acid, phosphate esters, fatty acids and salts and esters thereof, and the like. Such plasticizers are useful as compatibilizing materials as well as to improve the mechanical properties of the cellulose ether. Salts of fatty acids, particularly ammonium salts thereof, are of particular interest because such salts perform the three-fold function of plasticizing the cellulose ether, compatibilizing the active agent with the cellulose ether and stabilizing the dispersion. Dispersions employing fatty acid salts as stabilizers require a pH sufficiently high so that the fatty acid is maintained in the salt form. Fatty acid salts convert to the free acid form at low pH's, and thereby will fail to stabilize the dispersion. Therefore, such fatty acid salt-stabilized dispersions are generally not preferred when the active agent degrades in an alkaline medium.

In addition to the foregoing optional ingredients, the water-insoluble cellulose ether may be employed in conjunction with one or more other polymeric materials which may be employed for their particular beneficial properties. Said other polymers may be any which is compatible with, i.e., miscible with or soluble in the water-insoluble cellulose ether, including water-soluble cellulose ethers, such as methylcellulose, hydroxypropylcellulose, hydroxypropylmethylcellulose, carboxymethylhydroxyethylcellulose, polyacrylamides, polyacetates, and diverse cellulose esters, and the like.

The dispersions of this invention are advantageously prepared by the simple mixing of the active agent into the previously prepared dispersion of the water-insoluble, organophilic cellulose ether. The amount of active agent employed in preparing the dispersions of this invention is that amount which is desirably diffused into the cellulose ether particles. Upon mixing the active agent with the cellulose dispersion, agitation for a relatively short period, typically about five minutes to six hours, usually is effective to cause the diffusion of the active agent into the cellulose ether particles. Often, mild heating, (i.e., to a temperature of about 30°-80° C.) of the cellulose ether dispersion is necessary during the mixing of the active agent into the dispersion in order to obtain adequate diffusion of the active agent into the cellulose ether particles.

Once prepared, the dispersions of this invention may be employed in any desirable manner. For example, the dispersion may be sprayed or otherwise applied to the system to be treated with the active agent or may be incorporated with other ingredients (for example, a chewing gum base) to form a final product containing the active agent. Alternatively, the dispersion can be dewatered such as by centrifugation or spray drying to form a powder having sustained release properties. In addition, the cellulose ether particles may be coalesced using methods known in the art to form films or other articles having sustained release properties. The sustained release dispersions of this invention possess several advantages over conventional sustained release systems. The active agent is readily diffused into the cellulose ether particles. In contrast to matrix type sustained release systems, the active agent is more uniformly distributed throughout the cellulose ether particles. The physical form of the dispersion of this invention allows for a wide variety of uses not available to conventional sustained release systems. In addition, the compositions of the dispersion of this invention are readily adapted to tailor the dispersion for the desired end use.

The manner of use of the disperion of this invention depends largely on the particular active agent employed and the system to be treated therewith. For example, certain insecticides, such as chlorpyrifos are conveniently sprayed onto fields to remove insects therefrom. However, the chlorpyrifos is volatile and much of the chlorpyrifos evaporates before it penetrates the thatch covering the field. Accordingly, much of the chlorpyrifos is lost without acting on the insects. This loss of chlorpyrifos is decreased by employing a dispersion of this invention containing the chlorpyrifos as the active agent. The dispersion can be sprayed or otherwise applied to the field wet or as a dry powder. Because the chlorpyrifos is diffused into cellulose ether particles, the rate of evaporation thereof is greatly reduced. Moreover, chlorpyrifos-containing cellulose ether particles penetrate thatch more efficiently than chlorpyrifos itself. Thus, more of the chlorpyrifos reaches the areas to be treated and is therefore more effectively employed. Once the chlorpyrifos-containing dispersion of this invention penetrates the thatch, the chlorpyrifos is released by the gradual diffusion of the chlorpyrifos out of the particles and by the breaking down of the cellulose ether particles by enzymes and bacteria which reside in the soil.

The following examples are provided to illustrate the scope of the invention but not to limit the scope thereof. All parts and percentages are by weight unless otherwise indicated.

EXAMPLE 1

In this example, an aqueous dispersion containing 20 percent solids, having polymer particles containing 75 weight percent ethylcellulose, and 25 percent dibutylphthalate, is employed. The dispersion is stabilized using Calsoft 240 (an alkylaryl sulfonate salt) and ammonium hydroxide is dissolved into the aqueous phase To a 100-g portion of this dispersion is added 20 g of chlorpyrifos and 60 g of water. The mixture is agitated for 4 hours at 65° C. The product is a stable uniform dispersion.

The rate at which the chlorpyrifos evaporates from the dispersion is determined by the following procedure.

The above-prepared dispersion (Sample No. 1) is divided into 5 equal portions. One such portion is analyzed for chlorpyrifos. The 4 remaining portions are placed into an oven at 60° C. for 1 hour, 2 hours, 4 hours and 24 hours, respectively. Each sample is analyzed for chlorpyrifos after its removal from the oven and the amount of chlorpyrifos lost (based on the chlorpyrifos in the portion which is not heated) is calculated. For comparison (Sample No. C-1), four 12-gram portions of chlorpyrifos are also heated in an oven at 60° C. for 1, 2, 4 and 24 hours and the amount of material lost determined for each portion. The results are as given in Table I following.

TABLE I

| Sample | Percent Chlorpyrifos Lost at 60° C. | | | | |
|---|---|---|---|---|---|
| | 0 Hour | 1 Hour | 2 Hours | 4 Hours | 24 Hours |
| C-1* | 0 | 17 | 51 | 77 | 100 |
| 1 | 0 | 10 | 45 | 51 | 99 |

*Not an example of the invention

It can be seen from the foregoing table that the rate of loss of chlorpyrifos from the dispersion of this invention is significantly reduced as compared with the blank sample.

The relative ability of the chlorpyrifos-containing dispersion and pure chlorpyrifos to penetrate thatch is determined by the following procedure.

Five grams of pure long-filtered spaghum moss is soaked in 45 ml of tap water. The wet moss is placed into a funnel over a 4.25 inch diameter, 16 mesh wire screen, producing a thatch layer 1.5 cm thick. A sample of chlorpyrifos-containing ethylcellulose dispersion prepared as indicated in this example is diluted with water until the dispersion contains 4.5 milligrams of chlorpyrifos per 0.75 ml of dispersion (6000 ppm). A 0.75-ml portion of this dispersion is then sprayed onto the thatch and allowed to dry at room temperature for 30 minutes. After drying, 100 ml of tap water is sprayed onto the thatch. The water that penetrates the thatch in the first 30 minutes after application of the tap water is collected and analyzed for chlorpyrifos. A second 100-ml portion of tap water is sprayed onto the thatch, and the water penetrating the thatch is again collected for 30 minutes and analyzed for chlorpyrifos. The total amount of chlorpyrifos which penetrated the thatch is found to be 2.66 grams, or 59 percent of the chlorpyrifos contained in the dispersion sprayed onto the thatch.

For comparison, the experiment is repeated, this time using 0.75 ml of a 6000 ppm aqueous solution of chlorpyrifos alone (i.e., not contained in the aqueous dispersion of the invention). Only 29 percent of the chlorpyrifos is found to penetrate the thatch. Thus, it is seen that twice as much chlorpyrifos (59 percent versus 29 percent) penetrates the thatch when it is employed in the aqueous dispersion of the invention.

EXAMPLE 2

To 100 grams of a 20 weight percent solids aqueous dispersion of particles containing 75 weight percent ethylcellulose and 25 weight percent dibutylphthalate is added 20 grams nitrapyrin (a nitrogen stabilizer) and 60 grams water. This mixture is heated with agitation to 70° C. for 4 hours, then cooled to room temperature. On inspection, it is seen that all the nitrapyrin is diffused into the dispersed ethylcellulose polymers.

This product is heated at 30° C. in an open vessel. After 16 hours of heating, over 80 weight percent of the nitropyrin remains diffused within the ethylcellulose particles. An equivalent amount of pure nitrapyrin completely evaporates under the same conditions.

EXAMPLE 3

In this example, a dispersion containing particles of 75 weight percent ethylcellulose and 25 weight percent ricinoleic acid, stabilized with 3 grams octylphenoxy polyethoxyethanol surfactant and adjusted to pH 5.5 with HCl is employed. To 100 grams of this dispersion is added 7.5 grams of a 20 weight percent dibromonitrilopropionamide (DBNPA) solution in a tetraethylene glycol/water solvent system. The mixture is stirred at room temperature for 72 hours. All the DBNPA is diffused into the polymer particles.

What is claimed is:

1. A dispersion of plasticized, polymeric particles for the sustained release of an insecticide, said dispersion comprising:

(a) a continuous aqueous phase having dispersed therein, (b) a plurality of particles; which particles comprise (1) a water-insoluble thermoplastic cellulose ether polymer;

(2) a plasticizing composition comprising an amount of a water-soluble salt of a fatty acid, sufficient to stabilize the dispersion, said fatty acid being one which is a plasticizer for the cellulose ether polymer; and (3) an insecticide reversibly diffused into said particles wherein said insecticide is an organic compound or composition which exhibits a greater affinity for the cellulose ether than the aqueous phase.

2. The dispersion of claim 1, wherein said cellulose ether polymer is ethylcellulose or ethylhydroxypropyl methylcellulose.

3. A powder formed by dewatering the dispersion of claim 1.

4. A film or other article formed by the coalescence of the dispersion of claim 1.

5. The dispersion of claim 1 wherein the active agent is chlorpyrifos.

6. The powder of claim 3 wherein the active agent is chlorpyrifos.

7. The film or other article of claim 4 wherein the active agent is chlorpyrifos.

8. The dispersion of claim 2 wherein the active agent is chlorpyrifos.

9. A dispersion of plasticized, polymeric particles for the sustained release of an insecticide, the dispersion comprising:

(a) a continuous agueous phase having dispersed therein, (b) a plurality of particles such that the dispersion contains between about 5 and about 40 weight percent solids; which particles comprise (1) a water-insoluble thermoplastic cellulose ether polymer;

(2) a plasticizing composition comprising an amount of a water-soluble salt of a fatty acid sufficient to stabilize the dispersion, said fatty acid being one which is a plasticizer for the cellulose ether polymer; and (3) an insecticide reversibly diffused into the particles wherein said insecticide is an organic compound or composition which exhibits a greater affinity of the cellulose ether than the aqueous phase.

* * * * *